US012331012B2

(12) United States Patent
Ku et al.

(10) Patent No.: US 12,331,012 B2
(45) Date of Patent: Jun. 17, 2025

(54) ORGANIC CATALYST FOR NON-AQUEOUS ALDOL CONDENSATION

(71) Applicant: Dow Global Technologies LLC, Midland, MI (US)

(72) Inventors: Sung-Yu Ku, Lake Jackson, TX (US); Sally Demaio-Turner, Lake Jackson, TX (US); Wanglin Yu, Lake Jackson, TX (US); Michael A Brammer, Freeport, TX (US)

(73) Assignee: Dow Global Technologies LLC, Midland, MI (US)

( * ) Notice: Subject to any disclaimer, the term of this patent is extended or adjusted under 35 U.S.C. 154(b) by 360 days.

(21) Appl. No.: 17/999,978

(22) PCT Filed: May 27, 2021

(86) PCT No.: PCT/US2021/034461
§ 371 (c)(1),
(2) Date: Nov. 28, 2022

(87) PCT Pub. No.: WO2021/242987
PCT Pub. Date: Dec. 2, 2021

(65) Prior Publication Data
US 2023/0303473 A1    Sep. 28, 2023

Related U.S. Application Data

(60) Provisional application No. 63/032,147, filed on May 29, 2020.

(51) Int. Cl.
*C07C 45/45* (2006.01)
*B01J 27/24* (2006.01)
*B01J 31/02* (2006.01)
*C07C 45/49* (2006.01)

(52) U.S. Cl.
CPC ............... *C07C 45/49* (2013.01); *B01J 27/24* (2013.01); *B01J 31/0259* (2013.01)

(58) Field of Classification Search
CPC ................................ C07C 45/45; B01J 27/24
See application file for complete search history.

(56) References Cited

U.S. PATENT DOCUMENTS

| | | |
|---|---|---|
| 4,598,162 A | 7/1986 | Forster et al. |
| 5,663,452 A | 9/1997 | Kulmala et al. |
| 5,741,944 A | 4/1998 | Bryant et al. |
| 6,620,960 B2 | 9/2003 | Ekkundi et al. |
| 7,071,351 B2 | 7/2006 | Schmitt et al. |
| 7,119,234 B2 | 10/2006 | Kulkarni et al. |
| 7,169,749 B1 | 1/2007 | Friesenhagen et al. |
| 7,247,755 B2 | 7/2007 | Konishi et al. |
| 8,563,782 B2 | 10/2013 | Kaizik et al. |
| 9,035,075 B1 | 5/2015 | Lee et al. |
| 9,688,599 B2 * | 6/2017 | Kannan ............ C07C 45/74 |
| 2003/0022947 A1 | 1/2003 | Mcatee et al. |
| 2004/0138510 A1 | 7/2004 | Kramarz et al. |
| 2015/0299081 A1 | 10/2015 | Kannan et al. |
| 2017/0291866 A1 | 10/2017 | Kannan et al. |

FOREIGN PATENT DOCUMENTS

JP    2010/065020 A    3/2010

* cited by examiner

*Primary Examiner* — Sikarl A Witherspoon
(74) *Attorney, Agent, or Firm* — Boyle Fredrickson S.C.

(57) ABSTRACT

The present disclosure provides a process. In an embodiment, the process includes providing a first blend composed of nonanals, $C_8$ olefins and $C_7$-$C_9$ alkanes. The process includes adding, to the first blend, a component selected from $C_4$ aldehyde, $C_5$ aldehyde, and combinations thereof to form a non-aqueous reaction mixture having an initial water content from 0 wt % to 10 wt % water. The process includes introducing an organic base catalyst to the non-aqueous reaction mixture and heating the non-aqueous reaction mixture to a temperature from 30° C. to 100° C. and cross-aldol condensing the non-aqueous reaction mixture. The process includes forming a cross-aldol product composed of a component selected from $C_8$ enals, $C_{10}$ enals, $C_{13}$ enals, $C_{14}$ enals, and $C_{18}$ enals, and combinations thereof.

15 Claims, 4 Drawing Sheets

ORGANIC CATALYST FOR NON-AQUEOUS ALDOL CONDENSATION

BACKGROUND

Reclamation of the purged hydrocarbon species is one of the biggest challenges facing large scale polyolefin production. For example, conversion of the octene comonomer in ethylene/octene copolymer polymerization production is generally very low, for example between 10 and 20%. This means that 80-90% of the octene can pass through the reactor without being converted to polymer.

The hydroformylation of an octene/alkane industrial purge stream using a hydroformylation catalyst generates a mixture of $C_8$ aldehydes, unreacted $C_8$ olefins, and hydrocarbon solvent. This hydroformylation product can then be cross-aldol reacted with butyraldehyde and/or valeraldehyde to produce $C_8$-$C_{18}$ aldehydes. With subsequent hydrogenation, these $C_8$-$C_{18}$ aldehydes can then be used to produce $C_8$-$C_{18}$ alcohols. $C_8$-$C_{18}$ alcohols are high-demand starting materials for end applications such as surfactants, for example.

Industrial-scale cross-aldol condensation reactions are typically performed with an inorganic base catalyst, such as sodium hydroxide (NaOH), for example, dissolved in an aqueous solution. However, the use of inorganic base catalyst in aqueous solution is problematic when attempting to perform a cross-aldol reaction with the hydroformylation product made from purge stream composed octene isomers/alkane with butyraldehyde or valeraldehyde. The presence of the unreacted $C_8$ olefins and hydrocarbon solvent (alkanes) in the purge stream hydroformylation product produces a non-aqueous and non-polar environment for the aldol reaction. The $C_8$ aldehydes and the $C_4$ aldehyde or $C_5$ aldehyde are significantly different in polarity. Their relative solubility in water and in the mixture of alkanes and octenes is significantly different. $C_4$ aldehyde or $C_5$ aldehyde is more soluble in the aqueous phase than the $C_8$ aldehydes. This situation results in predominate self-condensation of the $C_4$ aldehyde or $C_5$ aldehyde instead of the desired cross-condensation between $C_4$ aldehyde or $C_5$ aldehyde and the $C_9$ aldehyde in the reaction. Adding a solvent such that the aldehydes become miscible with the inorganic base catalyst, e.g., isopropanol, can promote the cross-condensation reaction. However, solvents such as isopropanol can form multiple azeotropes in the aldol reaction product mixture, making it difficult to recover the organic solvent from the aldol reaction product.

In addition, using an inorganic base catalyst in the presence of a polar organic solvent requires high concentration of the inorganic base catalyst in order to achieve high conversions of the aldehyde reactants. High concentrations of inorganic base catalyst, however, typically results in undesired side reactions and undesired byproducts. The side reactions not only reduce the yields of the desired products, but also result in the formation of carboxylic acids through, for example, the Cannizzaro reaction. Carboxylic acids and their salts in the presence of unreacted olefins and hydrocarbon (such as would be present in a $C_8$ aldehyde product derived from a polymerization unit purge stream) can result in severe gelation. The gelation of the aldol reaction mixture is problematic because it is difficult to handle and makes further processing of the aldol reaction product costly, time consuming, and energy-consuming.

Hence, the art recognizes the need for a catalyst capable of driving the aldol reaction when a hydrophobic hydroformylation reaction product (e.g., nonanal) is used as starting material. Further desired is a catalyst that can produce an aldol reaction product containing little, or no, azeotropes and yields a room temperature-flowable product when a non-aqueous alkene/alkane hydroformylation reaction product is used as starting material.

SUMMARY

The present disclosure provides a process. In an embodiment, the process includes providing a first blend composed of nonanals, $C_8$ olefins, and $C_7$-$C_9$ alkanes. The process includes adding, to the first blend, a component selected from $C_4$ aldehyde, $C_5$ aldehyde, and combinations thereof to form a non-aqueous reaction mixture having an initial water content from 0 wt % to 10 wt % water. The process includes introducing an organic base catalyst to the non-aqueous reaction mixture and heating the non-aqueous reaction mixture to a temperature from 30° C. to 100° C. and cross-aldol condensing the non-aqueous reaction mixture. The process includes forming a cross-aldol product composed of a component selected from $C_8$ enals, $C_{10}$ enals, $C_{13}$ enals, $C_{14}$ enals, $C_{18}$ enals, and combinations thereof.

DEFINITIONS

Figure 1:
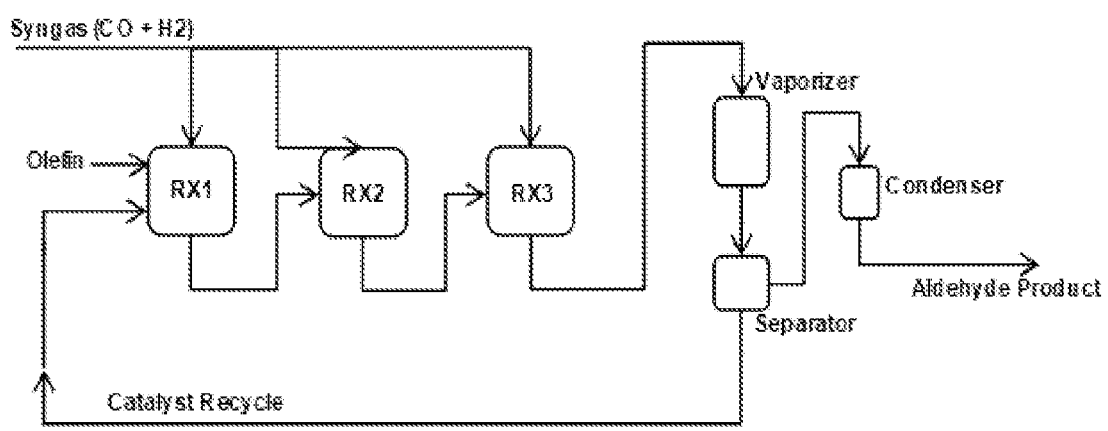
FIG. 1 is a schematic representation of a hydroformylation reactor system for providing hydroformylation conditions, in accordance with an embodiment of the present disclosure.

Any reference to the Periodic Table of Elements is that as published by CRC Press, Inc., 1990-1991. Reference to a group of elements in this table is by the new notation for numbering groups.

For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

The numerical ranges disclosed herein include all values from, and including, the lower and upper value. For ranges containing explicit values (e.g., 1 or 2, or 3 to 5, or 6, or 7), any subrange between any two explicit values is included (e.g., the range 1-7 above includes subranges of 1 to 2; 2 to 6; 5 to 7; 3 to 7; 5 to 6; etc.).

Unless stated to the contrary, implicit from the context, or customary in the art, all parts and percents are based on weight and all test methods are current as of the filing date of this disclosure.

An "alcohol" is a compound having a hydroxyl group (—OH) attached to a hydrocarbon radical.

An "aldehyde" is a compound having a carbonyl functional group (C=O) attached to one hydrocarbon radical and a hydrogen atom.

An "alkene" is a hydrocarbon containing a carbon-carbon double bond.

The terms "blend" or "polymer blend," as used herein, is a blend of two or more polymers. Such a blend may or may not be miscible (not phase separated at molecular level). Such a blend may or may not be phase separated. Such a blend may or may not contain one or more domain configurations, as determined from transmission electron spectroscopy, light scattering, x-ray scattering, and other methods known in the art.

The term "composition" refers to a mixture of materials which comprise the composition, as well as reaction products and decomposition products formed from the materials of the composition.

The terms "comprising," "including," "having" and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term "consisting essentially of" excludes from the scope of any succeeding recitation any other component, step, or procedure, excepting those that are not essential to operability. The term "consisting of" excludes any component, step, or procedure not specifically delineated or listed. The term "or," unless stated otherwise, refers to the listed members individually as well as in any combination. Use of the singular includes use of the plural and vice versa.

An "enal" is an aldehyde compound that contains a carbon-carbon double bond. Enals may be formed by aldol (or cross-aldol) condensation of aldehydes followed by dehydration of the resulting intermediate compound. A non-limiting example of an enal is 2-ethylhexenal, which results from the self-condensation of $C_4$ aldehyde as shown below:

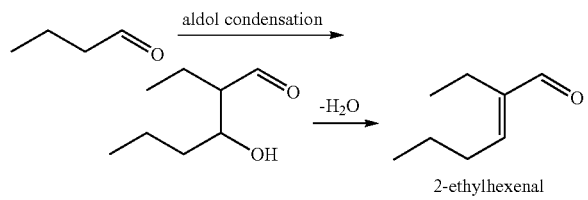

2-ethylhexenal

An "enol" is an alcohol which contains a carbon-carbon double bond. An enol may be formed by partial hydrogenation of an enal.

An "ethylene-based polymer" is a polymer that contains more than 50 weight percent (wt %) polymerized ethylene monomer (based on the total amount of polymerizable monomers) and, optionally, may contain at least one comonomer. Ethylene-based polymer includes ethylene homopolymer, and ethylene copolymer (meaning units derived from ethylene and one or more comonomers). The terms "ethylene-based polymer" and "polyethylene" may be used interchangeably.

A "hydrocarbon" is a compound containing only hydrogen atoms and carbon atoms. A "hydrocarbonyl" (or "hydrocarbonyl group") is a hydrocarbon having a valence (typically univalent).

The term "1-octene," as used herein, is an unsaturated hydrocarbon-olefin having the molecular formula $C_8H_{16}$ and the unsaturation is at the alpha position. 1-octene has the molecular Structure (A) as shown below.

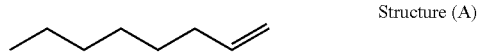

Structure (A)

The term "isomer of octene," as used herein, is an unsaturated hydrocarbon having the molecular formula $C_8H_{16}$, and the unsaturation (the double bond) is not at the alpha position. In other words, the term "isomer of octene" is any octene to the exclusion of 1-octene. Nonlimiting examples of isomers of octene include cis-2-octene, trans-2-octene, cis-3-octene, trans-3-octene, and combinations thereof as well as cis-4-octene, trans-4-octene, branched octene isomers and combinations of thereof.

The term "linear internal octene isomer" as used herein, is a linear and unsaturated hydrocarbon composed of an eight-carbon chain, and the unsaturation (the double bond) is not at the alpha position. Linear internal octene isomers include cis-2-octene, trans-2-octene, cis-3-octene, trans-3-octene, cis-4-octene, trans-4-octene, and combinations thereof. The term "branched $C_8$ olefin" as used herein is an unsaturated hydrocarbon having the molecular formula $C_8H_{16}$, and a main chain length of ≤7 carbon atoms. In contrast to the linear nature of Structure A, branched $C_8$ olefins contain at least one hydrocarbon radical directly bonded to the main chain. Nonlimiting examples of branched $C_8$ olefins include methylheptenes such as 3-methyl-2-heptene, 3-methyl-3-heptene, 5-methyl-2-heptene, 5-methyl-3-heptene, and the like. Additional nonlimiting examples of branched $C_5$ olefins include dimethylhexenes such as 3,4-dimethyl-2-hexene, 3,4-dimethyl-3-hexene, 2,3-dimethyl-3-hexene and the like. Further nonlimiting examples include ethylhexenes, such as 2-ethyl-1-hexene and the like.

An "olefin" is an unsaturated, aliphatic hydrocarbon having a carbon-carbon double bond.

A "polymer" is a compound prepared by polymerizing monomers, whether of the same or a different type, that in polymerized form provide the multiple and/or repeating "units" or "mer units" that make up a polymer. The generic term polymer thus embraces the term homopolymer, usually employed to refer to polymers prepared from only one type of monomer, and the term copolymer, usually employed to refer to polymers prepared from at least two types of monomers. It also embraces all forms of copolymer, e.g., random, block, etc. The terms "ethylene/α-olefin polymer" and "octene/α-olefin polymer" are indicative of copolymer as described above prepared from polymerizing ethylene or octene respectively and one or more additional, polymerizable α-olefin monomer. It is noted that although a polymer is often referred to as being "made of" one or more specified monomers, "based on" a specified monomer or monomer type, "containing" a specified monomer content, or the like, in this context the term "monomer" is understood to be referring to the polymerized remnant of the specified monomer and not to the unpolymerized species. In general, polymers herein are referred to as being based on "units" that are the polymerized form of a corresponding monomer.

TEST METHODS

Gas Chromatography (GC).

The composition of the spent solvent and the hydroformylation reaction product is determined by Gas Chromatography (GC) using the following conditions:

| | |
|---|---|
| Instrument | Agilent Technologies Model 7890 with Flame Ionization Detector |
| Data System | Agilent OpenLab A.02.01 |
| Injector Inlet | 270° C. using 4 mm split/splitless liner with glass wool PN 092002 |
| Column mode: Ramped Pressure | 20 psi (hold for 10 min.) ramp at 0.5 psi/min to 30 psi (hold 1 min.) ramp at 1 psi/min to 50 psi (hold 49 min.) |
| Mode | Split |
| Split Ratio | 150:1 |
| Injection Volume | 1 µL |
| Column | Supelco Petrocol DH 100 m × 0.25 mm i.d. × 0.5 µm |
| Oven Ramp. | 40° C. (Hold 40 min.) Ramp at 10° C./min. to 220° C. (hold 5 minutes) Ramp at 5° C./min. to 260° C. (hold 19 min.) Ramp at 5° C./min. to 270° C. (hold 48 min.) |
| Run Time | 140 minutes |
| Detector | FID set at 270° C. |
| FID Hydrogen Flow | 40 mL/min. |
| FID Air Flow | 400 mL/min. |
| Nitrogen (Make-up) gas flow | 20 mL/min. |

Quantitation for this data of Table 1 and Section A in the Examples section is based on weight percent using response factors derived from standard solutions at known concentration.

The compositions of the cross-aldol reaction product is determined by GC using the following conditions:

| | |
|---|---|
| Instrument | Agilent Technologies Model 6890 with Flame Ionization Detector and 5973 MSD |
| Data System | Agilent Enhanced Chemstation D.01.02.16 |
| Injector Inlet | 250° C. using 4 mm split/splitless liner with glass wool PN 092002 |
| Column mode: Constant flow | Constant Flow at 2 mL/min |
| Mode | Split |
| Split Ratio | 50:1 |
| Injection Volume | 1 µL |
| Column | Agilent VF-17MS 30 m × 0.32 m × 0.25 µm |
| Oven Ramp. | 30° C. (Hold 2.20 min.) Ramp at 10° C./min. to 330° C. (hold 2 minutes) |
| Run Time | 34.20 Minutes |
| Detector | FID set at 250° C. |
| FID Hydrogen Flow | 40 mL/min. |
| FID Air Flow | 450 mL/min. |
| Nitrogen (Make-up) gas flow | 45 mL/min. |
| MSD Source Temp: | 230°C |
| MSD Quad Temp: | 150° C. |
| MSD Tune: | STune |
| MSD Scan Parameters: | Scan 30-500 m/z |
| Library: | NIST MS Search 2.0f, build Oct. 22, 2009 |

Quantitation in the Examples section is based on GC area percent from the FID signal (interchangeably referred to as "GC area," or "GC %"). Confirmation of peak identities/component structure is based on the Electron Ionization Mass Selective Detector signal matched to the National Institute of Standards and Testing library.

N:I ratio. Hydroformylation reactions of olefins with three or more carbon atoms produce a mixture of both linear and branched isomers. The term "N:I ratio," as used herein, is the ratio of linear or normal (N) aldehyde isomer to the branched or isoaldehyde (I) isomer. The N:I ratio is calculated by dividing the concentration of the normal aldehyde (wt %) by the concentration of the isoaldehyde (wt %). The weight percent concentration of each aldehyde isomer is determined by Gas Chromatography (GC).

Turbidity is measured using a Hach Ratio Turbidimeter with a range of 0-200 NTU. Measurements are taken at room temperature using an 8 dram sample cell. The calibration of the instrument was confirmed using Gelex Turbidity Standards. Each sample was allowed to equilibrate for at least 15 seconds for the reading to stabilize. If the sample had any phase separation, the organic phase is measured. the organic phase mixture. Results are reported in Nephelometric Turbidity Units (NTU).

DETAILED DESCRIPTION

The present disclosure provides a process. The process includes providing a first blend composed of nonanals, $C_8$ olefins and $C_7$-$C_8$ alkanes and adding, to the first blend, a component selected from $C_4$ aldehyde, $C_5$ aldehyde, and combinations thereof to form a non-aqueous reaction mixture. The non-aqueous reaction mixture has an initial water content from 0 wt % to 10 wt % water. The process includes introducing an organic base catalyst to the non-aqueous reaction mixture. The process includes heating the non-aqueous reaction mixture to a temperature from 30° C. to 100° C. and cross-aldol condensing the non-aqueous reaction mixture. The process includes forming a cross-aldol product composed of a component selected from $C_8$ enals, $C_{10}$ enals, $C_{13}$ enals, $C_{14}$ enals, and $C_{18}$ enals, and combinations thereof.

The process includes providing a first blend composed of, or otherwise consisting of, nonanals, $C_8$ olefins, and $C_7$-$C_8$ alkanes and contains 0 wt %, or greater than 0 wt % to 10 wt % water, or from 0 wt %, or greater than 0 wt % to 8 wt % water. In an embodiment, the first blend is the reaction product of the hydroformylation of a purge steam. A "purge stream," as used herein, is one of several fractions separated, or otherwise recovered, from the effluent that exits a polymerization reactor after a polymerization reaction has occurred. The liquid effluent exiting the polymerization reactor contains solid (granular) polymer product, which is removed. A recycle stream is also removed from the effluent which is further processed and returned to the polymerization reactor. The purge stream is the stream that remains (i) after the polymer product has been recovered from the effluent and (ii) after the recycle stream has been separated from the effluent. The purge stream contains unreacted olefin monomer(s), including octene isomers, and other hydrocarbons utilized during the polymerization reaction. It is understood that the purge stream contains no, or substantially no, solid polymer product therein.

In an embodiment, the purge stream is effluent from a polymerization reactor in which ethylene is co-polymerized with octene. The purge stream includes unreacted octene isomers and other hydrocarbons.

In an embodiment, the purge stream includes
(i) from 20 wt % to 55 wt %, or from 25 wt % to 50 wt % 1-octene,
(ii) from 20 wt % to 60 wt % linear internal octene isomers,
(iii) from 2 wt % to 8 wt % branched $C_8$ olefins; and
(iv) from 5 wt % to 60 wt % hydrocarbon solvent, wherein weight percent is based on total weight of the purge stream. It is understood the components (i)-(iv) amount to 100 weight percent of the purge stream.

The purge stream is fed into a hydroformylation reactor system. In the hydroformylation reactor system, the hydroformylation reaction bonds a formyl group (—CH=O) and a hydrogen atom to a carbon-carbon double bond of an alkene (i.e., olefin) to produce aldehyde. As the purge stream contains octene isomers, subjecting the purge stream to hydroformylation conditions forms a reaction product composed of nonanals. A "nonanal" is an aldehyde containing nine carbon atoms. The purge stream is a mixture of alkenes (primarily octene isomers) and alkanes, consequently the reaction product from the hydroformylation reaction includes other components in addition to the nonanals. Nonlimiting examples of other components in the hydroformylation reaction product include $C_8$ olefins, $C_7$-$C_9$ alkanes, and combinations thereof.

The process includes adding, to the first blend (the first blend containing nonanals, $C_8$ olefins and $C_7$-$C_9$ alkanes), a component selected from a $C_4$ aldehyde, a $C_5$ aldehyde, and combinations thereof (hereafter "$C_4$/$C_5$ aldehyde") to form a non-aqueous reaction mixture having an initial water content from 0 wt % to 8 wt % water. The initial water content is from 0 wt %, or greater than 0 wt % to 10 wt % water, or 0 wt %, or from greater than 0 wt % to 8 wt % water, or from 1 wt % to 8 wt % water, or from greater than 0 wt % to 6 wt % water, or from 1 wt % to 4 wt % water. In an embodiment, the initial water content is from 0 wt %, or greater than 0 wt % to 10 wt % water, or from 0 wt %, or greater than 0 wt % to 8 wt % water, or from 0 wt %, or greater than 0 wt % to 6 wt % water, or from 0 wt %, or greater than 0 wt % to 4 wt % water. Weight percent is based on total weight of the non-aqueous reaction mixture.

The process includes introducing an organic base catalyst to the non-aqueous reaction mixture. An "organic base catalyst," as used herein, is a compound composed of (i) an alkyl ammonium cation or an alkyl phosphonium cation, wherein the alkyl moiety is a $C_{10}$-$C_{30}$ hydrocarbonyl group (or a $C_{10}$-$C_{20}$ hydrocarbonyl group), the organic base catalyst also including (ii) an anion that is a hydroxyl group (—OH) or a halo-group (—Cl, —Br). The anion can be a hydroxyl group (—OH) bound to the cation, or the hydroxide anion can be generated in situ in a reaction mixture containing inorganic base catalyst, such as sodium hydroxide (NaOH) and/or potassium hydroxide (KOH). Nonlimiting examples of suitable organic base catalyst include tetrabutylammonium hydroxide (TBAH), tributylmethylammonium hydroxide (TBMAH), tetrabutylphosphonium hydroxide (TBPH), tetrabutylammonium bromide, and combinations thereof.

In an embodiment, the organic base is introduced into a basic reaction mixture containing NaOH and/or KOH. The inorganic base catalyst-to-organic base catalyst ratio is from 0.1-1:1. In other words, the present process uses the organic base catalyst to reduce, or to significantly reduce, the amount of inorganic base catalyst (NaOH and/or KOH) in the reaction mixture.

In an embodiment, the organic base is introduced into the reaction mixture to the exclusion of inorganic base catalyst such as sodium hydroxide and/or potassium hydroxide. In other words, the present process uses the organic base catalyst as the sole catalyst, thereby avoiding, or otherwise eliminating, the presence of an inorganic base (such as sodium hydroxide and/or potassium hydroxide) in the process.

Once the organic base catalyst is introduced to the non-aqueous reaction mixture, the process includes heating the non-aqueous reaction mixture to a temperature from 30° C. to 100° C., or to a temperature from 40° C. to 70° C., or to a temperature from 50° C. to 60° C., and cross-aldol condensing the non-aqueous reaction mixture. In the cross-aldol condensing step, the organic base catalyst catalyzes the aldehyde-alcohol condensation to form the cross-aldol product and the by-product of condensed water. The cross-aldol product is composed of enals selected from $C_8$ enals, $C_{10}$ enals, $C_{13}$ enals, $C_{14}$ enals, $C_{18}$ enals, and combinations thereof. The cross-aldol product may further include the alcohol solvent, water, unreacted aldehydes, other $C_8$, $C_{10}$, $C_{13}$, $C_{14}$, $C_{18}$ species, and combinations thereof. In an embodiment, the cross-aldol product includes a majority amount of $C_8$ enals, $C_{10}$ enals, $C_{13}$ enals, $C_{14}$ enals, $C_{18}$, wherein "majority amount" is greater than 50% of the total GC area for the cross-aldol reaction product The term "species," as used herein, is a mixture of alcohols, enals, enols, and aldehydes, wherein each alcohol, enal, enol, and aldehyde in the species has the same number of carbon atoms. A "$C_8$ species" is a mixture of $C_8$ alcohols, $C_8$ enals, $C_8$ enols, and $C_8$ aldehydes. A "$C_{10}$ species" is a mixture of $C_{10}$ alcohols, $C_{10}$ enals, $C_{10}$ enols and $C_{10}$ aldehydes. A "$C_{13}$ species" is a mixture of $C_{13}$ alcohols, $C_{10}$ enals, $C_{13}$ enols and $C_{13}$ aldehydes. A "$C_{14}$ species" is a mixture of $C_{14}$ alcohols, $C_{14}$ enals, $C_{14}$ enols and $C_{14}$ aldehydes. A "$C_{18}$ species" is a mixture of $C_{18}$ alcohols, $C_{18}$ enals, $C_{18}$ enols and $C_{18}$ aldehydes.

The process includes forming a cross-aldol product that is a flowable liquid at 23° C. and has a turbidity value less than 1.0 NTU, or from 0 NTU, or greater than 0 NTU to 1.0 NTU. Utilization of inorganic base catalyst (e.g., NaOH) in the presence of (i) low initial water content (0-10 wt % initial water), (ii) olefins, and (iii) alkanes produces a cross-aldol product that is a non-flowing gel at 23° C. and has a turbidity greater than 200 NTU. Applicant discovered that use of the organic base catalyst in the presence of (i) low initial water content (0-10 wt % initial water), (ii) olefins, and (iii) alkanes unexpectedly produces a cross-aldol product that is flowable at 23° C. and has a turbidity less than 1.0 NTU. In an embodiment, the process includes forming a cross-aldol product that is a flowable liquid at 23° C. and has a turbidity value from 0 NTU to 1.0 NTU, or from greater than 0 NTU to 0.9 NTU, or from 0.05 NTU to 0.5 NTU.

In an embodiment, the process includes adding $C_4$ aldehyde to the first blend to form the non-aqueous reaction mixture (with initial water content of 0-10 wt %). The process includes introducing the organic base catalyst (TBAH) at an organic base catalyst-to-total aldehyde molar ratio from 0.0036-0.0286:1, and forming a cross-aldol product composed of enals selected from $C_8$ enals, $C_{13}$ enals, $C_{18}$ enals, and combinations thereof. The cross-aldol product may further include the alcohol solvent, water, unreacted aldehydes, other $C_8$, $C_{13}$, and $C_{18}$ species (in addition to the aforementioned enals). The cross-aldol product includes a majority amount of $C_5$ enals, $C_{13}$ enals, and $C_{18}$ enals, wherein "majority amount" is greater than 50% of the total GC area for the cross-aldol reaction product. The cross-aldol product is flowable at 23° C. and has a turbidity from 0 NTU to 1.0 NTU, or from greater than 0 NTU to 0.9 NTU, or from 0.05 NTU to 0.5 NTU. The $C_4$ aldehyde and/or $C_9$ aldehyde conversion rate to $C_8/C_{13}/C_{18}$ species is from 90% to 99%, or from 92% to 98%, or from 93% to 97%.

In an embodiment, the process includes adding $C_5$ aldehyde to the first blend to form the non-aqueous reaction mixture (with initial water of 0-8 wt %). The process includes introducing the organic base catalyst (TBAH) at an organic base-to-total aldehyde molar ratio from 0.0036-0.0286:1, and forming a cross-aldol composed of enals selected from $C_{10}$ enals, $C_{14}$ enals, $C_{18}$ enals, and combinations thereof. The cross-aldol product may further include the alcohol solvent, water, unreacted aldehydes and other $C_{10}$, $C_{14}$, $C_{18}$ species (in addition to the aforementioned enals). The cross-aldol product includes a majority amount of $C_{10}$ enals, $C_{14}$ enals, and $C_{18}$ enals, wherein "majority amount" is greater than 50% of the total GC area for the cross-aldol reaction product. The cross-aldol product is flowable at 23° C. and has a turbidity from 0 NTU to 1.0 NTU, or from greater than 0 NTU to 0.9 NTU, or from 0.05 NTU to 0.5 NTU. The $C_5$ aldehyde and/or $C_9$ aldehyde conversion rate to $C_{10}/C_{14}/C_{18}$ species is from 90% to 99%, or from 92% to 98%, or from 93% to 97%.

By way of example, and not limitation, some embodiments of the present disclosure will now be described in detail in the following Examples.

EXAMPLES

The composition of purge stream recovered from an ethylene/octene polymerization production process is provided in Table 1 below.

TABLE 1

| Purge stream | (wt %) |
| --- | --- |
| hydrocarbon solvent | 6.1 |
| branched C9 olefins | 4.8 |
| 1-octene | 42.4 |

TABLE 1-continued

| Purge stream | (wt %) |
| --- | --- |
| trans-4-octene | 2.4 |
| trans-3-octene and cis-4-octene (co-elution) | 9.9 |
| cis-3-octene | 2.0 |
| octane | 0.6 |
| trans-2-octene | 17.0 |
| cis-2-octene | 14.8 |

Ligands for the hydroformylation catalyst used in the inventive examples (IE) are provided in Table 2 below.

TABLE 2

Ligand A for hydroformylation catalyst, for Hydroformylation 1

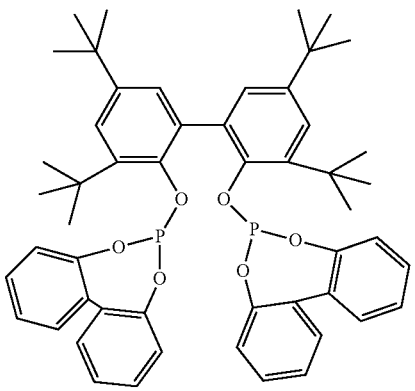 [SMILES: CC(C)(C)c1cc(-c2cc(C(C)(C)C)cc(C(C)(C)C)c2Op2oc3ccccc3c3ccccc3o2)c(Op2oc3ccccc3c3ccccc3o2)c(C(C)(C)C)c1]

6,6'-[[3,3',5,5'-tetrakis(I, 1-dimethylethyl)-[1,1'-biphenyl]-2, 2'-diyl]bis(oxy) ]bis-dibenzo[d,f] [1,3,2]-dioxaphosphepin Ligand B for hydroformylation catalyst, for Hydroformylation 2

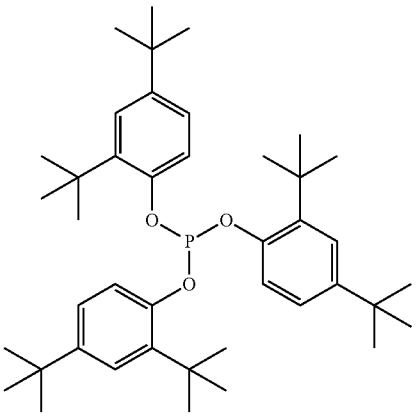 [SMILES: CC(C)(C)c1ccc(OP(Oc2ccc(C(C)(C)C)cc2C(C)(C)C)Oc2ccc(C(C)(C)C)cc2C(C)(C)C)c(C(C)(C)C)c1]

A. Subjecting Purge Stream to Hydroformylation Conditions (Hydroformylation 1)

Hydroformylation conditions are provided in a reactor system as shown in FIG. 1. The reactor system consists of three 1-liter stainless steel stirred tank reactors (Rx 1, Rx 2, Rx 3) connected in series. Each reactor is equipped with a vertically mounted agitator and a circular tubular sparger near the bottom for feeding the olefin and/or syngas to the reactor. The sparger contains a plurality of holes of sufficient size to provide the desired gas flow into the liquid body. Each reactor has a silicone oil shell as a way to control reactor temperature. Reactors 1 to 2 and reactors 2 to 3 are further connected via lines to transfer any unreacted gases and to allow a portion of the liquid solution containing aldehyde product and catalyst to flow (e.g. via pressure differential or by pumping) from reactor 1 to reactor 2 and from reactor 2 to reactor 3. Hence, the unreacted olefin of reactor 1 is further hydroformylated in reactor 2 and subsequently in reactor 3. In an alternate configuration, Reactor 3 (Rx 3) may be bypassed, such that only two reactors are employed.

Each reactor also contains a pneumatic liquid level controller for maintaining the desired liquid levels in the reactors. Reactor 1 further contains a line for introducing olefin, carbon monoxide and hydrogen through the sparger while makeup carbon monoxide and hydrogen are passed to reactors 2 and 3 via a transfer line that also carries the unreacted gases from reactor 1 to reactor 2 and from reactor 2 to reactor 3. Each reactor also includes a blow-off vent for controlled removal of unreacted gases if desired. A portion of the liquid reaction solution is continuously pumped from the final reactor in series to a vaporizer, which consists of a heated zone wherein a stream of flowing gas (strip gas) is utilized to sweep a portion of the volatile components to a water-cooled condenser where they can be collected as a liquid in a product receiver (crude product). The non-volatiles are passed through an aqueous extraction zone which consists of a contacting region and a separation zone. The purpose of the aqueous extraction is to extract acidic byproducts, thereby preventing additional hydrolysis of the phosphite ligands, as described in U.S. Pat. No. 5,741,944. Following the aqueous extraction, the organic non-volatiles are pumped through a recycle line back into reactor 1.

A purge stream is introduced into Reactor 1 ("olefin" in FIG. 1 represents the purge stream). The purge stream is from an ethylene-octene polymerization production process/ The composition of the purge stream is provided in Table 1, above.

The hydroformylation reaction is conducted using two Reactors (Rx 1 and Rx 2 with Rx 3 being by-passed). Two-liters of catalyst solution composed of rhodium dicarbonyl acetylacetonate (394 ppm rhodium), ligand A (Table 2 above) (0.7 wt. %; 2.0 mole equivalents ligand A per mole rhodium), tetraethylene glycol dimethyl ether (about 15% by weight) and mixed $C_4$ aldehyde (about 85% by weight: n-butyraldehyde to iso-butyraldehyde ratio of about 30:1) is charged to the reactor system shown in FIG. 1. The reactors are then heated to 70° C. under flowing syn gas ($CO:H_2$ ratio=1:1). Reactor 1 and 2 pressures are maintained at 244 and 220 psig respectively. The spent solvent is fed to Reactor 1 at a rate of 138 grams per hour. The vaporizer system is operated with a strip gas comprised of 1:1 syn gas at a flow rate of 790 sLph; the vaporizer pressure is maintained at 7 psig with a catalyst temperature of 101° C.

After several days of continuous operation, the butyraldehydes and tetraethylene glycol dimethyl ether are removed overhead leaving a reactor process fluid composed of nonanals, aldehyde heavies (byproducts of in situ aldol condensation), unreacted olefins and hydrocarbon solvent (continually introduced as part of the spent solvent). The reaction product composed of nonanals (nonanals reaction product) is collected at a rate of 155 grams/hour. The composition of the nonanals reaction product is shown in Table 3 below.

B. Subjecting purge stream to hydroformylation conditions (Hydroformylation 2)

Hydroformylation conditions are provided in the 2-reactor system as shown in FIG. 1 and described in Hydroformylation 1, above. Two-liters of catalyst solution composed of rhodium dicarbonyl acetylacetonate (150 ppm rhodium), Ligand B (0.75 wt. %; 7.0 mole equivalents per mole rhodium), and the $C_9$ aldehyde product from Example 1A is charged to the mini-plant. The reactors are then heated to 90° C. under flowing syn gas ($CO:H_2$ ratio=1:1). Reactor 1 and 2 pressures are maintained at 472 and 438 psig respectively. The spent solvent is fed to Reactor 1 at a rate of 175 grams per hour. The vaporizer system is operated with a strip gas comprised of 1:1 syn gas at a flow rate of 790 sLph; the vaporizer pressure is maintained at 7 psig with a catalyst temperature of 100-105° C. The $C_9$ aldehyde product is collected at a rate of 212 grams/hour; the composition is shown in Table 3.

TABLE 3

Composition of nonanals reaction product.

| | Hydroformylation 1 wt. % | Hydroformylation 2 |
|---|---|---|
| $C_9$ aldehydes | 64.8 | 89.2 |
| unreacted $C_8$ olefins | 32.8 | 6.7 |
| hydrocarbon solvent | 2.4 | 4.1 |
| N:I ratio of the $C_9$ aldehydes | 13.8:1 (93.2% n-nonanal) | 0.44:1 (30.6% n-nonanal) |

C. Cross-Aldol Condensation 1-dodecane is used as the GC internal standard to calculate $C_4$ and $C_8$ conversion. The master batch of butyraldehyde containing 1 mol % internal standard is prepared with a mixture of 1-dodecane (17 g, 0.1 mol) and butyraldehyde (720 g, 10.0 mol). The master batch of butyraldehyde is used for the later cross aldol chemistry. $C_4$ and $C_9$ aldehyde conversions are calculated between raw material mixture feed of $C_4$ and $C_9$ aldehydes and a product mixture using the GC method. GC area integration/1-dodecane are used to evaluate the product yield. For example, $C_8$/1-dodecane area ratio represents $C_8$ product yield, $C_{13}$/1-dodecane area ratio represents $C_{13}$ product yield, $C_{18}$/1-dodecane area ratio represent $C_{18}$ product yield, total $(C_8+C_{13}+C_{18})$/1-dodecane represents $C_8$, $C_{13}$ and $C_{18}$ product yield.

i. Comparative Sample (CS) A

Comparative sample A is a cross-aldol condensation reaction of the nonanals reaction product from hydroformylation 1 (Table 3 above) with butyraldehyde catalyzed $NaOH_{(aq)}$. A mixture of butyraldehyde (25.3 g; 0.350 mol) and nonanals reaction product from hydroformylation 1 (38.2 g; 0.175 mol n-nonanal) is prepared and loaded into a 300 ml Parr reactor, purged with nitrogen three times, and sealed under nitrogen. A solution of NaOH catalyst (1.2 g; 30 mmol) and water (42 g) is prepared and added into the Parr reactor using a Gilson pump at a feed rate of 20 mL/min at 30° C. After the addition, the reaction mixture is heated to 60° C. under vigorous stirring, and the temperature is maintained at 60° C. for 60 minutes. The reaction mixture is cooled to 40° C. and quenched with 0.9 equivalents of acetic acid. The neutralized reaction mixture is transferred to a separatory funnel and the organic phase is collected. The conversion of butyraldehyde and nonanal, and product yield of $C_8$, $C_{13}$, and $C_{18}$ enals are calculated from gas chromatography, the weight % of initial water is calculated, and results are provided in Table 5.

ii. Comparative Sample B, Comparative Sample C

Isopropanol (21 g) and a quantity of NaOH that is specified in Table 5 are charged into to a 300 mL Parr reactor, purged with nitrogen three times, and sealed. The solution is heated to 60° C. with vigorous stirring. A mixture of $C_4$ aldehydes (0.175 mol, 12.6 g) and nonanals reaction product from hydroformylation 1 (Table 3 above) (0.0875 mol, 22.2 g) is prepared, analyzed using GC, and introduced to the reactor with a small lab pump at a feed rate of 40 mL/minute. After addition, the temperature is maintained at the 60° C. reaction temperature with stirring for 1 hour. The reaction mixture is then cooled to 40° C. and immediately analyzed using GC. Once cooled to room temperature, the reaction mixtures are analyzed for turbidity and photographed to illustrate the liquid or gel behavior.

Figure 2A:
FIG. 2A is a photograph of the cross-aldol product from comparative sample B, with container in an upright position.
Figure 2B:
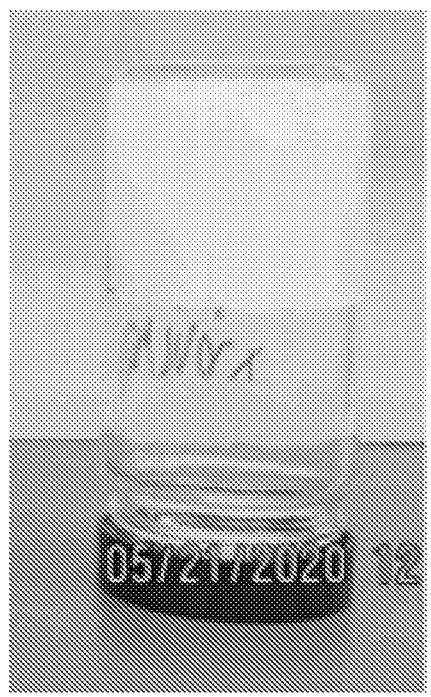
FIG. 2B is a photograph of the cross-aldol product from comparative sample B, with container in an inverted position.
Figure 3A:
FIG. 3A is a photograph of the cross-aldol product from comparative sample C, with container in an upright position.
Figure 3B:
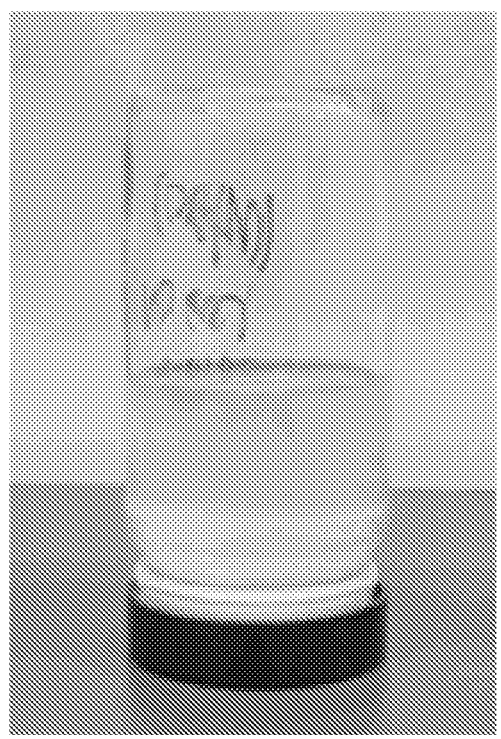
FIG. 3B is a photograph of the cross-aldol product from comparative sample C, with container in an inverted position.

In Comparative sample B, a slightly cloudy liquid reaction mixture is obtained. Gelation is observed visually for comparative sample B as shown in the photograph in FIG. 2A, comparative sample B is a gel. Comparative sample B is not flowable even when the container is turned upside down (subjected to inversion), as shown in the photograph in FIG. 2B. The turbidity for comparative sample B is measured to exceed 200 NTU.

Comparative sample C is not a gel, and the mixture is flowable. However, product yield is low $C_4$ conversion 21%, $C_8$ conversion 33%. Comparative sample C also has high turbidity (greater than 1 NTU), comparative sample C having a turbidity of 36 NTU.

Figure 4A:
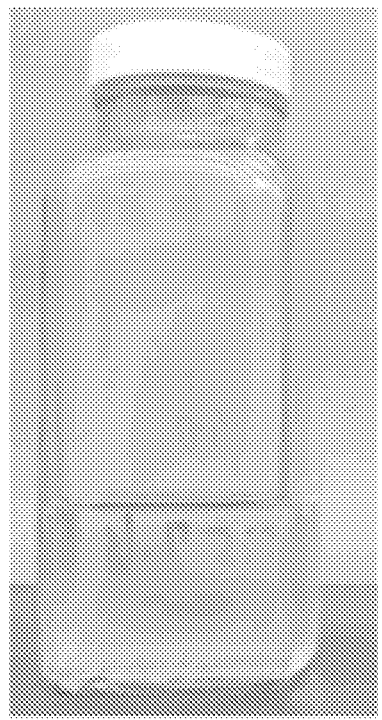
FIG. 4A is a photograph of the cross-aldol product from inventive example 2d, with container in an upright position.
Figure 4B:
FIG. 4B is a photograph of the cross-aldol product from inventive example 2d, with container in an inverted position.

(iii) Inventive Examples (IE) 2a-2d: Homogeneous Cross-Aldol Condensation Reaction of Nonanals Reaction Product from Hydroformylation 1 with Varying Amounts of TBAH Catalyst A mixture of butyraldehyde (25.3 g; 0.350 mol) and nonanals reaction product from hydroformylation 1 (Table 3 above) (38.2 g; 0.175 mol n-nonanal) is prepared and loaded into a 300 mL Parr reactor, purged with nitrogen three times, and sealed under nitrogen. The 40 wt % of TBAH aqueous solution (quantity specified in Table 5) is prepared and added into the Parr reactor using a Gilson pump at a feed rate of 20 mL/min at 30° C. After the addition, the reaction mixture is heated to 60° C. under vigorous stirring, and the temperature is maintained at 60° C. for 60 minutes. The reaction mixture is cooled to 40° C. and quenched with 0.9 equivalents of acetic acid. The neutralized reaction mixture is transferred to a separatory funnel and the organic phase is collected. The conversion of butyraldehyde and nonanal, and product yield of $C_8$, $C_{13}$, and $C_{18}$ enals are calculated from gas chromatography, the weight % of initial water is calculated and results are summarized in Table 5. Inventive example 2a-2d each is flowable without any gelation. FIG. 4A is a photograph showing IE 2d in a container in an upright position. When the container holding IE 2d is inverted, shown in the photograph and FIG. 4B, IE 2d flows downward to cover the container cap of the upside down container. Inventive example 2a-2d each has low turbidity (less than 1.0 NTU), IE 2a turbidity value is 0.14 NTU, IE 2b turbidity value is 0.12 NTU, IE 2c turbidity value is 0.13 NTU, and IE 2d turbidity value is 0.12 NTU.

(iv) Inventive Example 3: Homogeneous Cross-Aldol Condensation Reaction of Nonanals Reaction Product from Hydroformylation 1 with Tetrabutyl Ammonium Bromide+NaOH Catalyst A mixture of butyraldehyde (25.3 g; 0.350 mol) and nonanals reaction product from hydroformylation 1 (Table 3 above) (38.2 g; 0.175 mol n-nonanal) is prepared and loaded into a 300 mL Parr reactor, purged with nitrogen three times, and sealed under nitrogen. A mixed catalyst solution of tetrabutylammonium bromide (3.8 mmol, 1.21 g) and NaOH (3.8 mmol, 0.15 g) dissolved in water (3 g) is prepared and added into the Parr reactor using a Gilson pump at a feed rate of 20 ml/min at 30° C. . . . . After the addition, the reaction mixture is heated to 60° C. under vigorous stirring, and the temperature is maintained at 60° C. for 60 minutes. The reaction mixture is cooled to 40° C. and quenched with 0.9 equivalents of acetic acid. The neutralized reaction mixture is transferred to a separatory funnel and the organic phase is collected. The conversion of butyraldehyde and nonanal, and product yield of $C_8$, $C_{13}$, and $C_{18}$ enals are calculated from gas chromatography, the weight % of initial water is calculated, and results are provided in Table 5. Inventive example 3 is flowable without any gelation. IE3 has low turbidity (less than 1.0 NTU), the turbidity value for IE3 is 0.15 NTU.

(v) Inventive Example 4: Cross-Aldol Condensation Reaction with $C_4$ Aldehyde and Branched $C_8$ Isomers to Generate $C_8$-$C_{18}$ Aldol Products A mixture of butyraldehyde (25.3 g; 0.350 mol) and nonanals reaction product from hydroformylation 2 (Table 3 above) (38.2 g; 0.175 mol n-nonanal) is prepared and loaded into a 300 mL Parr reactor, purged with nitrogen three times, and sealed under nitrogen. The 40 wt % of TBAH aqueous solution (15 mmol, 9.73 g) is added into the Parr reactor using a Gilson pump at a feed rate of 20 mL/min at 30° C. After the addition, the reaction mixture is heated to 60° C. under vigorous stirring, and the temperature is maintained at 60° C. for 60 minutes. The reaction mixture is cooled to 40° C. and quenched with 0.9 equivalents of acetic acid. The neutralized reaction mixture is transferred to a separatory funnel and the organic phase is collected. The conversion of butyraldehyde, nonanal, branched $C_9$ aldehydes and product yield of $C_8$, $C_{13}$, and $C_{18}$ enals are calculated from gas chromatography, the weight % of initial water is calculated, and results are provided in Table 5. Inventive example 4 is flowable without any gelation. IE4 has low turbidity (less than 1.0 NTU), the turbidity value for IE4 is 0.09 NTU.

IE4 demonstrates that the TBAH catalyst not only converts the linear $C_4$ aldehyde and $C_8$ aldehyde conversion to greater than 98% (99%), but also branched $C_9$ aldehyde conversion to greater than 60% (62%).

TABLE 5

Cross-aldol reaction process, product, and properties

| | Base | Base/total aldehydes molar ratio | Weight % initial water | Gelation | Organic phase Turbidity (NTU) | $C_4$ conversion (%) | $C_9$ conversion (%) | $C_8$ enal (GC %) | $C_{13}$ enal (GC %) | $C_{18}$ enal (GC %) | Total $C_8$ + $C_{13}$ + $C_{18}$ |
|---|---|---|---|---|---|---|---|---|---|---|---|
| CS A | NaOH(aq) | 0.0571 | 39 | No | 4.10 | 97 | 16 | 24.3 | 2.1 | 0.6 | 27 |
| CS B | NaOH in IPA | 0.0571 | 0 | Yes | >200 | 83 | 89 | 10.5 | 14.7 | 3.8 | 29 |
| CS C | NaOH in IPA | 0.0072 | 0 | No | 36 | 21 | 33 | 2.6 | 3.5 | 0.7 | 6.8 |

TABLE 5-continued

Cross-aldol reaction process, product, and properties

|  | Base | Base/total aldehydes molar ratio | Weight % initial water | Gelation | Organic phase Turbidity (NTU) | $C_4$ conversion (%) | $C_9$ conversion (%) | $C_8$ enal (GC %) | $C_{13}$ enal (GC %) | $C_{18}$ enal (GC %) | Total $C_8 + C_{13} + C_{18}$ |
|---|---|---|---|---|---|---|---|---|---|---|---|
| IE 2a | TBAH(aq) | 0.0286 | 8 | No | 0.14 | 99 | 98 | 13.9 | 21.8 | 7.6 | 43.3 |
| IE 2b | TBAH(aq) | 0.0143 | 4 | No | 0.12 | 98 | 97 | 14.8 | 22.8 | 6.2 | 43.9 |
| IE 2c | TBAH(aq) | 0.0072 | 2 | No | 0.13 | 96 | 93 | 15.8 | 22.1 | 6.5 | 44.4 |
| IE 2d | TBAH(aq) | 0.0036 | 1 | No | 0.12 | 96 | 92 | 15.4 | 24.4 | 7.7 | 47.5 |
| IE 3 | TBAB + NaOH(aq) | 0.0072 | 4 | No | 0.15 | 97 | 95 | 13.6 | 22.7 | 7.8 | 44.1 |
| IE 4 | TBAH (aq) | 0.0286 | 10 | No | 0.09 | 99 | 98* | 11.1 | 12.7 | 0.9 | 24.7 |

*Branched $C_9$ conversion is 62%

It is specifically intended that the present disclosure not be limited to the embodiments and illustrations contained herein, but include modified forms of those embodiments including portions of the embodiments and combinations of elements of different embodiments as come within the scope of the following claims.

The invention claimed is:

1. A process comprising:
providing a first blend comprising nonanals, $C_8$ olefins and $C_7$-$C_9$ alkanes;
adding, to the first blend, a component selected from the group consisting of $C_4$ aldehyde, $C_5$ aldehyde, and combinations thereof to form a non-aqueous reaction mixture having an initial water content from 0 wt % to 10 wt % water;
introducing an organic base catalyst to the non-aqueous reaction mixture;
heating the non-aqueous reaction mixture to a temperature from 30° C. to 100° C. and cross-aldol condensing the non-aqueous reaction mixture; and
forming a cross-aldol product composed of a component selected from the group consisting of $C_8$ enals, $C_{10}$ enals, $C_{13}$ enals, $C_{14}$ enals, and $C_{18}$ enals, and combinations thereof.

2. The process of claim 1 comprising forming a cross-aldol product having a turbidity value from 0 NTU to less than 1.0 NTU.

3. The process of claim 1 comprising forming a cross-aldol product that is flowable at 23° C.

4. The process of claim 1 comprising introducing the organic base catalyst at an organic base catalyst-to-total aldehyde molar ratio from 0.0036-0.0286:1.

5. The process of claim 1 comprising introducing an organic base catalyst selected from the group consisting of tetrabutylammonium hydroxide, tributylmethylammonium hydroxide, tetrabutylphosphomium hydroxide, tetrabutylammonium bromide, and combinations thereof.

6. The process of claim 1 comprising forming the cross-aldol product in the absence of an inorganic base.

7. The process of claim 1 comprising
adding a $C_4$ aldehyde to the first blend to form the non-aqueous reaction mixture;
introducing the organic base catalyst at an organic base catalyst-to-total aldehyde molar ratio from 0.0036-0.0286:1; and
forming a cross-aldol product composed of a component selected from the group consisting of $C_8$ enals, $C_{13}$ enals, and $C_{18}$ enals, and combinations thereof.

8. The process of claim 1 comprising
adding a $C_5$ aldehyde to the first blend to form the non-aqueous reaction mixture;
introducing the organic base catalyst at an organic base catalyst-to-total aldehyde molar ratio from 0.0036-0.0286:1; and
forming a cross-aldol product composed of a component selected from the group consisting of $C_{10}$ enals, $C_{14}$ enals, and $C_{18}$ enals, and combinations thereof.

9. The process of claim 1 comprising
forming the cross-aldol product composed of (i) $C_{18}$ enals and (ii) a component selected from the group consisting of $C_8$ enals, $C_{10}$ enals, $C_{13}$ enals, $C_{14}$ enals, and combinations thereof.

10. The process of claim 1 comprising
forming the cross-aldol product composed of (i) $C_{18}$ enals, (ii) $C_{13}$ enals, and (iii) a component selected from the group consisting of $C_8$ enals, $C_{10}$ enals, $C_{14}$ enals, and combinations thereof.

11. The process of claim 10 comprising
forming the cross-aldol product composed of (i) $C_{18}$ enals, (ii) $C_{14}$ enals, and (iii) a component selected from the group consisting of $C_8$ enals, $C_{10}$ enals, $C_{13}$ enals, and combinations thereof.

12. The process of claim 9 wherein the organic base catalyst is selected from the group consisting of tetrabutylammonium hydroxide, tributylmethylammonium hydroxide, tetrabutylphosphomium hydroxide, and combinations thereof.

13. The process of claim 9 wherein the organic base catalyst consists of tetrabutylammonium bromide and sodium hydroxide.

14. The process of claim 7 comprising
forming the cross-aldol product composed of (i) $C_{18}$ enals and (ii) a component selected from the group consisting of $C_8$ enals, $C_{10}$ enals, $C_{13}$ enals, $C_{14}$ enals, and combinations thereof.

15. The process of claim 8 comprising
forming the cross-aldol product composed of (i) $C_{18}$ enals and (ii) a component selected from the group consisting of $C_8$ enals, $C_{10}$ enals, $C_{13}$ enals, $C_{14}$ enals, and combinations thereof.

* * * * *